US009307992B2

(12) United States Patent
Wilson et al.

(10) Patent No.: US 9,307,992 B2
(45) Date of Patent: Apr. 12, 2016

(54) BLOOD VESSEL TRANSECTING AND ANASTOMOSIS

(71) Applicant: C. R. Bard, Inc., Murray Hill, NJ (US)

(72) Inventors: Peter M. Wilson, Killingworth, CT (US); Alan B. Bachman, Milford, CT (US)

(73) Assignee: C.R. Bard, Inc., Murray Hill, NJ (US)

( * ) Notice: Subject to any disclaimer, the term of this patent is extended or adjusted under 35 U.S.C. 154(b) by 531 days.

(21) Appl. No.: 13/708,673

(22) Filed: Dec. 7, 2012

(65) Prior Publication Data

US 2013/0096585 A1  Apr. 18, 2013

Related U.S. Application Data

(63) Continuation of application No. 11/284,752, filed on Nov. 21, 2005, now Pat. No. 8,328,797.

(60) Provisional application No. 60/638,808, filed on Dec. 23, 2004.

(51) Int. Cl.

| A61B 17/08 | (2006.01) |
|---|---|
| *A61B 17/11* | (2006.01) |
| *A61B 17/32* | (2006.01) |
| A61B 18/14 | (2006.01) |
| A61B 17/00 | (2006.01) |

(52) U.S. Cl.
CPC ......... *A61B 17/11* (2013.01); *A61B 17/320016* (2013.01); *A61B 18/1492* (2013.01); *A61B 2017/00504* (2013.01); *A61B 2017/1107* (2013.01); *A61B 2017/1135* (2013.01); *A61B 2017/1139* (2013.01); *A61B 2017/32004* (2013.01)

(58) Field of Classification Search
CPC ........... A61B 17/11; A61B 17/320016; A61B 2017/1107; A61B 2017/1135; A61B 2017/1139; A61B 2017/1132; A61B 2017/32004
USPC .................. 606/204, 158, 157, 159, 185, 153
See application file for complete search history.

(56) References Cited

U.S. PATENT DOCUMENTS

| 3,837,345 | A |  | 9/1974 | Matar |  |
|---|---|---|---|---|---|
| 5,171,255 | A | * | 12/1992 | Rydell | ........................ 606/170 |
| 5,366,463 | A |  | 11/1994 | Ryan |  |
| 5,601,580 | A |  | 2/1997 | Goldberg et al. |  |
| 5,830,224 | A |  | 11/1998 | Cohn et al. |  |
| 6,022,313 | A |  | 2/2000 | Ginn et al. |  |
| 6,080,170 | A | * | 6/2000 | Nash et al. | .................... 606/159 |
| 6,099,542 | A |  | 8/2000 | Cohn et al. |  |
| 6,126,658 | A |  | 10/2000 | Baker |  |
| 6,132,429 | A |  | 10/2000 | Baker |  |
| 6,193,653 | B1 |  | 2/2001 | Evans et al. |  |
| 6,231,587 | B1 |  | 5/2001 | Makower |  |

(Continued)

OTHER PUBLICATIONS

U.S. Appl. No. 11/284,752, filed Nov. 21, 2005 Final Office Action dated Jun. 22, 2011.

(Continued)

*Primary Examiner* — Kathleen Holwerda
*Assistant Examiner* — Sarah Simpson
(74) *Attorney, Agent, or Firm* — Rutan & Tucker, LLP

(57) ABSTRACT

Method and device for cutting a blood vessel using a cutting tool from within the blood vessel. A first cut portion of the blood vessel is fused to a second blood vessel to provide a flow channel therebetween.

8 Claims, 8 Drawing Sheets

(56) References Cited

U.S. PATENT DOCUMENTS

| | | |
|---|---|---|
| 6,338,724 B1 | 1/2002 | Dossa |
| 6,398,797 B2 | 6/2002 | Bombard et al. |
| 6,464,665 B1 | 10/2002 | Heuser |
| 6,464,702 B2 | 10/2002 | Schulze et al. |
| 6,468,227 B2 | 10/2002 | Zimmon |
| 6,482,217 B1 | 11/2002 | Pintor et al. |
| 6,551,314 B1 | 4/2003 | Hill et al. |
| 6,551,334 B2 | 4/2003 | Blatter et al. |
| 6,551,335 B1 | 4/2003 | Bardeau et al. |
| 6,558,313 B1 | 5/2003 | Knighton et al. |
| 6,652,549 B1 | 11/2003 | Welten |
| 6,699,245 B2 | 3/2004 | Dinger et al. |
| 6,942,675 B1 | 9/2005 | Vargas |
| 8,328,797 B2 | 12/2012 | Wilson et al. |
| 2001/0007069 A1 | 7/2001 | Bombard et al. |
| 2002/0032462 A1 | 3/2002 | Houser et al. |
| 2002/0077637 A1 | 6/2002 | Vargas et al. |
| 2003/0032968 A1 | 2/2003 | Kirsch et al. |
| 2003/0040765 A1 | 2/2003 | Breznock |
| 2003/0097126 A1 | 5/2003 | Woloszko et al. |
| 2003/0129382 A1 | 7/2003 | Treat |
| 2003/0171775 A1 | 9/2003 | Belson |
| 2004/0059280 A1 | 3/2004 | Makower et al. |
| 2004/0073238 A1 | 4/2004 | Makower |
| 2004/0092960 A1* | 5/2004 | Abrams et al. .............. 606/139 |
| 2004/0097988 A1 | 5/2004 | Gittings et al. |
| 2004/0116946 A1 | 6/2004 | Goldsteen et al. |
| 2004/0181244 A1 | 9/2004 | Lee |
| 2006/0030935 A1 | 2/2006 | Scholz et al. |
| 2006/0100648 A1 | 5/2006 | Roy et al. |
| 2006/0142788 A1 | 6/2006 | Wilson et al. |
| 2006/0217706 A1 | 9/2006 | Lau et al. |
| 2006/0287657 A1 | 12/2006 | Bachman |
| 2007/0239117 A1 | 10/2007 | Chelak et al. |
| 2007/0265613 A1 | 11/2007 | Edelstein et al. |

OTHER PUBLICATIONS

U.S. Appl. No. 11/284,752, filed Nov. 21, 2005 Final Office Action dated Sep. 22, 2009.
U.S. Appl. No. 11/284,752, filed Nov. 21, 2005 Final Office Action dated Sep. 5, 2008.
U.S. Appl. No. 11/284,752, filed Nov. 21, 2005 Non-Final Office Action dated Dec. 11, 2007.
U.S. Appl. No. 11/284,752, filed Nov. 21, 2005 Non-Final Office Action dated Feb. 3, 2009.
U.S. Appl. No. 11/284,752, filed Nov. 21, 2005 Non-Final Office Action dated Nov. 1, 2010.
U.S. Appl. No. 11/284,752, filed Nov. 21, 2005 Notice of Allowance dated Aug. 15, 2012.

* cited by examiner

BLOOD VESSEL TRANSECTING AND ANASTOMOSIS

CROSS-REFERENCE TO RELATED APPLICATIONS

This application is a continuation of U.S. patent application Ser. No. 11/284,752, filed Nov. 21, 2005, now U.S. Pat. No. 8,328,797, which claims the benefit under 35 U.S.C. §119(e), to U.S. Provisional Application No. 60/638,808, filed Dec. 23, 2004, each of which is incorporated by reference into this application as if fully set forth herein.

BACKGROUND OF THE INVENTION

Patients suffering from reduced renal function or renal failure often have to undergo hemodialysis treatments. During dialysis, blood is withdrawn from the patient and is circulated through a hemodialysis machine. The machine removes toxic waste products and returns the purified blood to the patient. Typically, dialysis treatments are performed three times a week for the duration of a patient's life unless a kidney transplant procedure occurs. To successfully undergo hemodialysis treatment, blood is typically circulated through the hemodialysis machine at approximately 150 to 600 ml/minute flow rate for about 3-4 hours. Blood flow from the venous system is inadequate to meet the required flow rate and repeated punctures of large arteries are not feasible. Therefore, native fistulas are often created to provide blood flow access for the hemodialysis machines.

Typically, a native fistula is created by transecting a vein in the wrist near the back of the hand, freeing the vein from its connective tissue, bringing the vein around to the palm side of the wrist adjacent an artery, and affixing an anastomosis to connect the vessels with an open lumen to join the vein to the artery. The result is advantageous with a vein having significantly more blood flow than normal that can be used for exchanging large volumes of blood during dialysis. The surgeon performs the procedure by opening the skin surgically over the chosen area and completing the procedure externally to connect the vessels. However, such a procedure can be quite invasive, resulting in increased risk of adverse events to the patient.

It is therefore desirable to provide a procedure and device which creates a native fistula with a minimum of surgical intervention, which is less invasive and less traumatic to the patient than the presently utilized procedures.

BRIEF SUMMARY OF THE INVENTION

Accordingly, the present invention is directed to a method of blood vessel transecting and anastomosis comprising inserting a cutting tool into a first blood vessel, cutting the first blood vessel using the cutting tool from within the first blood vessel to separate the first blood vessel into a first cut portion and a second cut portion, and fusing the first cut portion of the first blood vessel to a second blood vessel to provide a flow channel between the first cut portion of the first blood vessel and the second blood vessel.

The fusing step may fuse the sides of the first and second blood vessels, or may fuse the end of the first cut portion of the first blood vessel to the side of the second blood vessel. The end of the second cut portion is sealed, and if the fusing is side to side, the end of the first cut portion is also sealed. The fusing step may be performed by radiofrequency (RF) energy, and sealing of the cut ends of the first blood vessel may also be performed by RF energy. In one variation, the first blood vessel is a vein and the second blood vessel is an artery. While the typical location for this procedure is in the wrist area of a patient, other bodily locations can be effectively used and are within the scope of this invention. The blood vessels to be connected may be advantageously located adjacent one another, but it should be understood by one of skill in the art with the benefit of the present disclosure that the procedure described herein can effectively move the first cut portion of the first blood vessel to a position adjacent the second blood vessel even if the second blood vessel is remote from the first blood vessel.

In one embodiment, the device for transecting a blood vessel comprises a cutting tool for insertion within a blood vessel, including a cutting means operative to transect the blood vessel, said cutting tool including a first closed position and a second open position, wherein the cutting means is exposed to the blood vessel internal surface for cutting in the open position and shielded from the blood vessel internal surface in the closed position.

These and other embodiments, features and advantages of the present invention will become more apparent to those skilled in the art when taken with reference to the following more detailed description of the invention in conjunction with the accompanying drawings that are first briefly described.

DETAILED DESCRIPTION OF THE INVENTION

The following detailed description should be read with reference to the drawings, in which like elements in different drawings are identically numbered. The drawings, which are not necessarily to scale, depict selected preferred embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Figure 1:
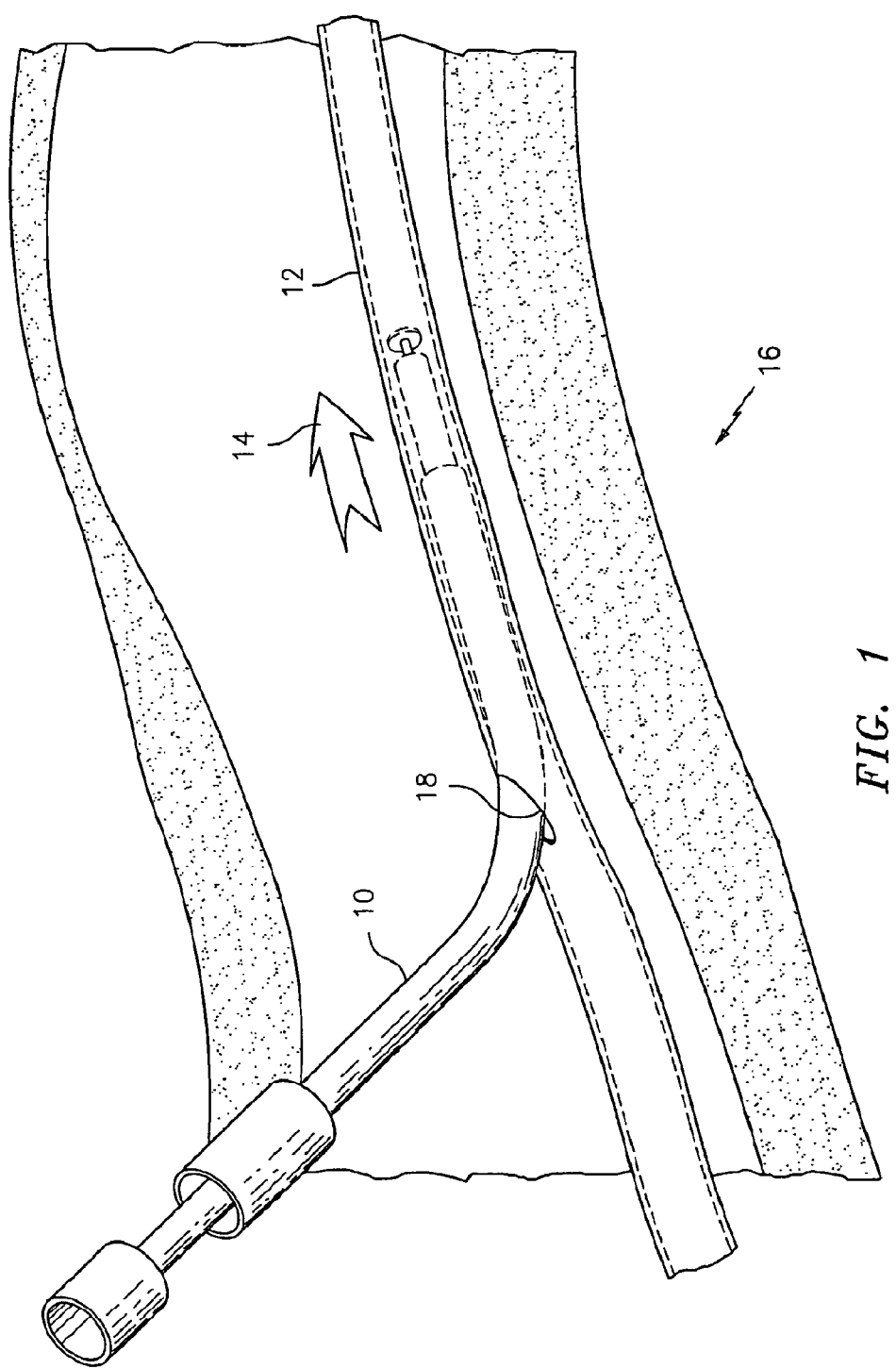
FIG. 1 is an illustration showing access to a vein in the forearm.
Figure 2:
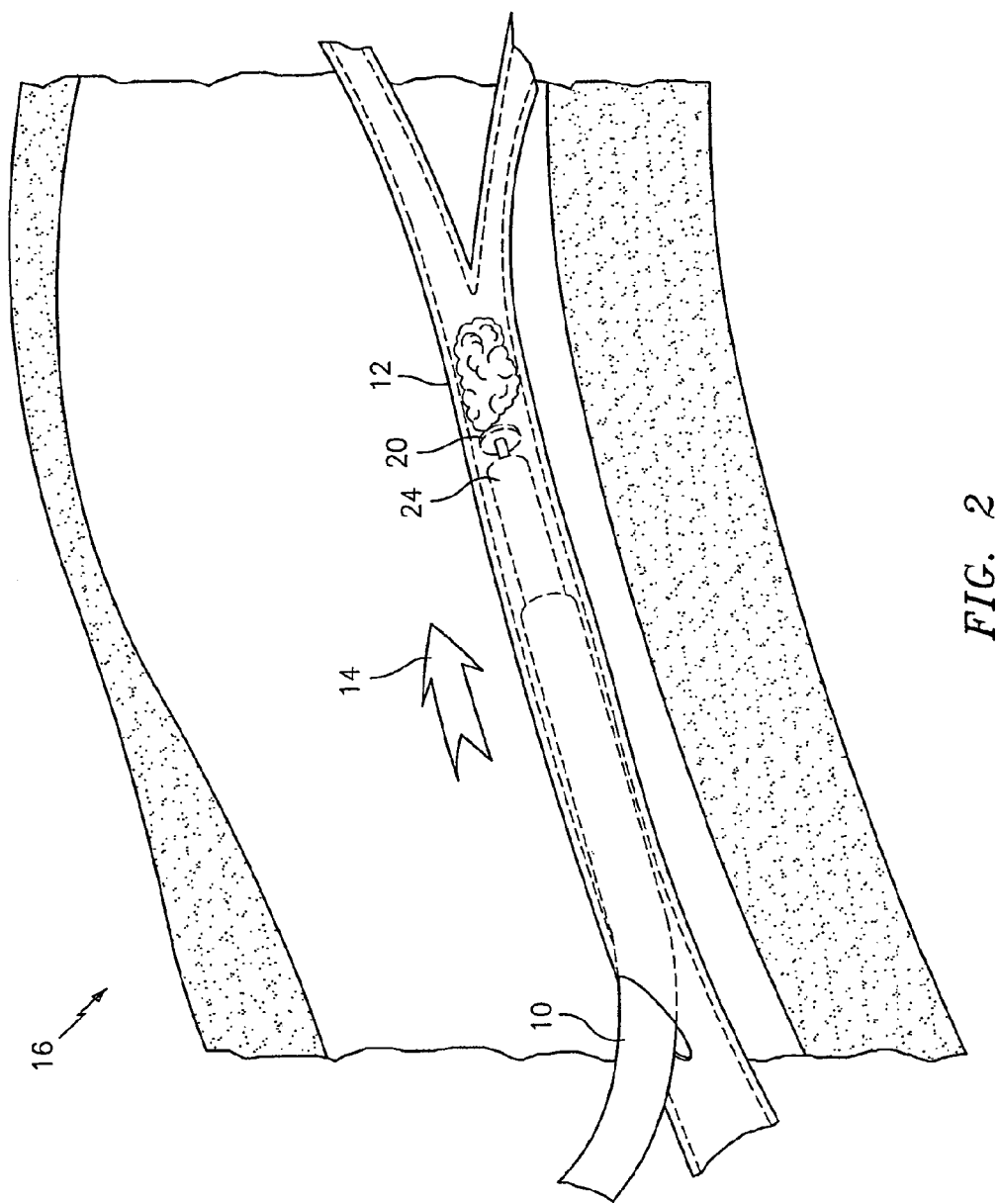
FIG. 2 shows the insertion of an occlusion device in the vein and deployment thereof to occlude the vein.
Figure 3:
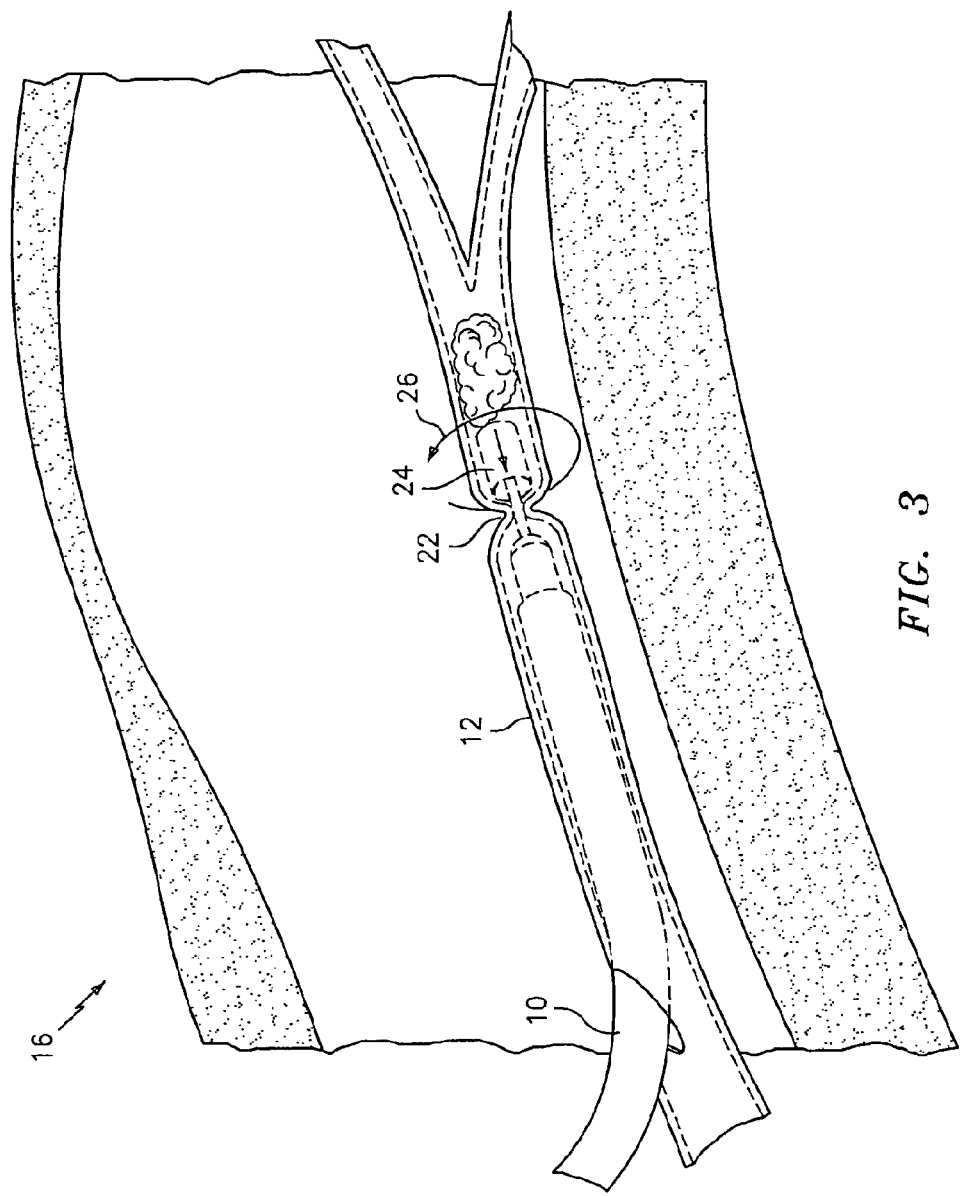
FIG. 3 shows rotation and operation of the occlusion device within the vein to transect the vein.

According to one embodiment of the present invention, a first phase in creating a native fistula is the transection of a desired vein using an appropriate cutting device. In one variation, the vein transecting device employs a cylindrical cutter to slice through the vein wall from within the vein, allowing for minimal surgical invention. As illustrated in FIGS. 1-3, a catheter 10 is inserted through a small incision 18 into a patient's vein 12 in the forearm or wrist 16 thereof in a direction 14 towards the patient's fingers. In this example, an occlusion device 20 is inserted through catheter 10 to occlude the vein as shown in FIG. 2, and a cutter 22 is inserted through the catheter 10 to perform the transection, as shown in FIG. 3. The forward end 24 of the catheter is closed to protect the cutter 22, and opened as shown in FIG. 3 when the cutting is to commence to expose the cutter. Suction or vacuum may be applied through the catheter to pull the vein wall towards the cutter, and the cutter rotated in either direction, such as in the direction of arrow 26, to sever the vein in the desired location. The suction or vacuum which may be applied, may be applied through an inner lumen of the catheter shaft and serves to pull the vein into the path of the rotating, cylindrical cutter.

Figure 7:
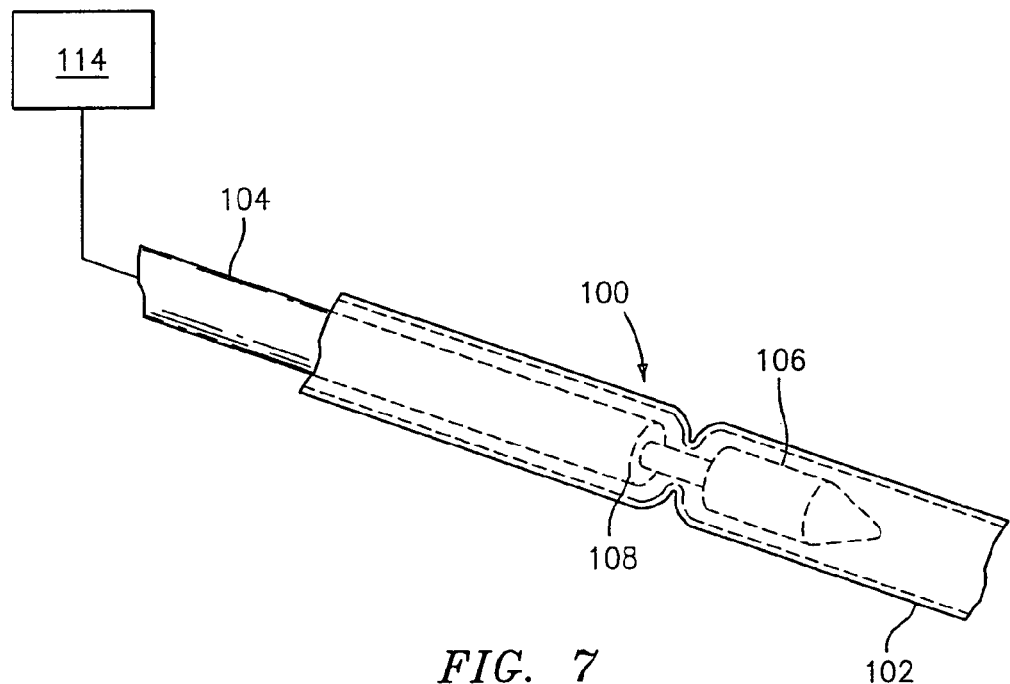
FIG. 7 is a detail view of the deployed catheter with cutting means exposed.
Figure 8:
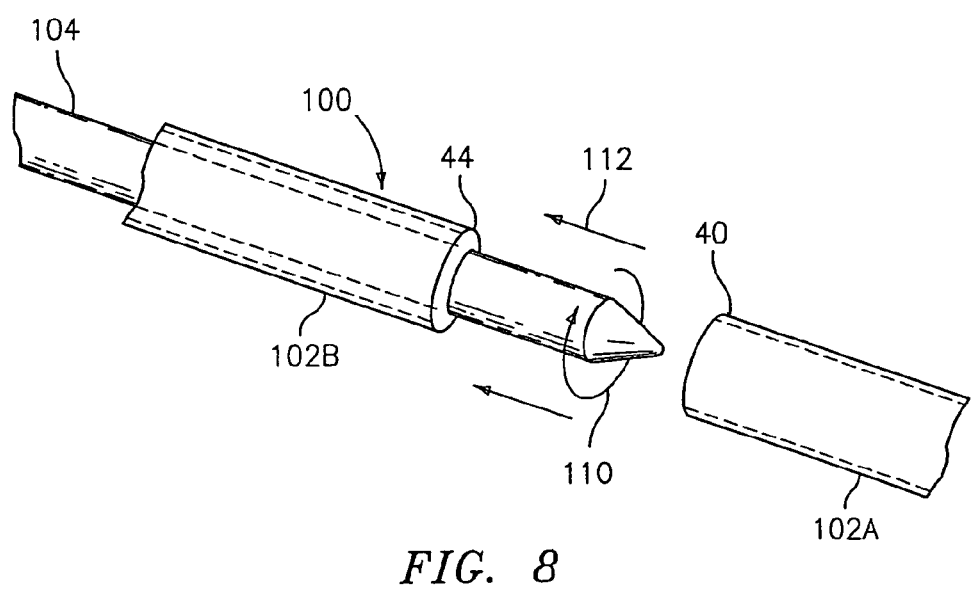
FIG. 8 is a detail view similar to FIG. 7 with the catheter closed to cover the cutting means.

The procedure for transecting a vein is further illustrated in FIGS. 7 and 8, which show a detailed view of a representative cutter 100, vein 102, catheter shaft 104, cutting means 106 and anvil 108. In the cutter open position shown in FIG. 7, vacuum or suction is applied through the catheter shaft 104 via vacuum or suction means 114, shown schematically, to pull the vein 102 inward. The cutting means 106 is rotated, such as in the direction of arrow 110 shown in FIG. 8, to cut the vein against the anvil 108 and to retract the cutter against the anvil. The vacuum or suction means is then shut off and the cutting device removed from within the vein in the direction of arrow 112, possibly with the cutting device including a cut segment of the vein. The resultant cut vein has two cut portions, first cut end portion 102A and second cut end portion 102B, as can be seen in FIG. 8.

Figure 4:
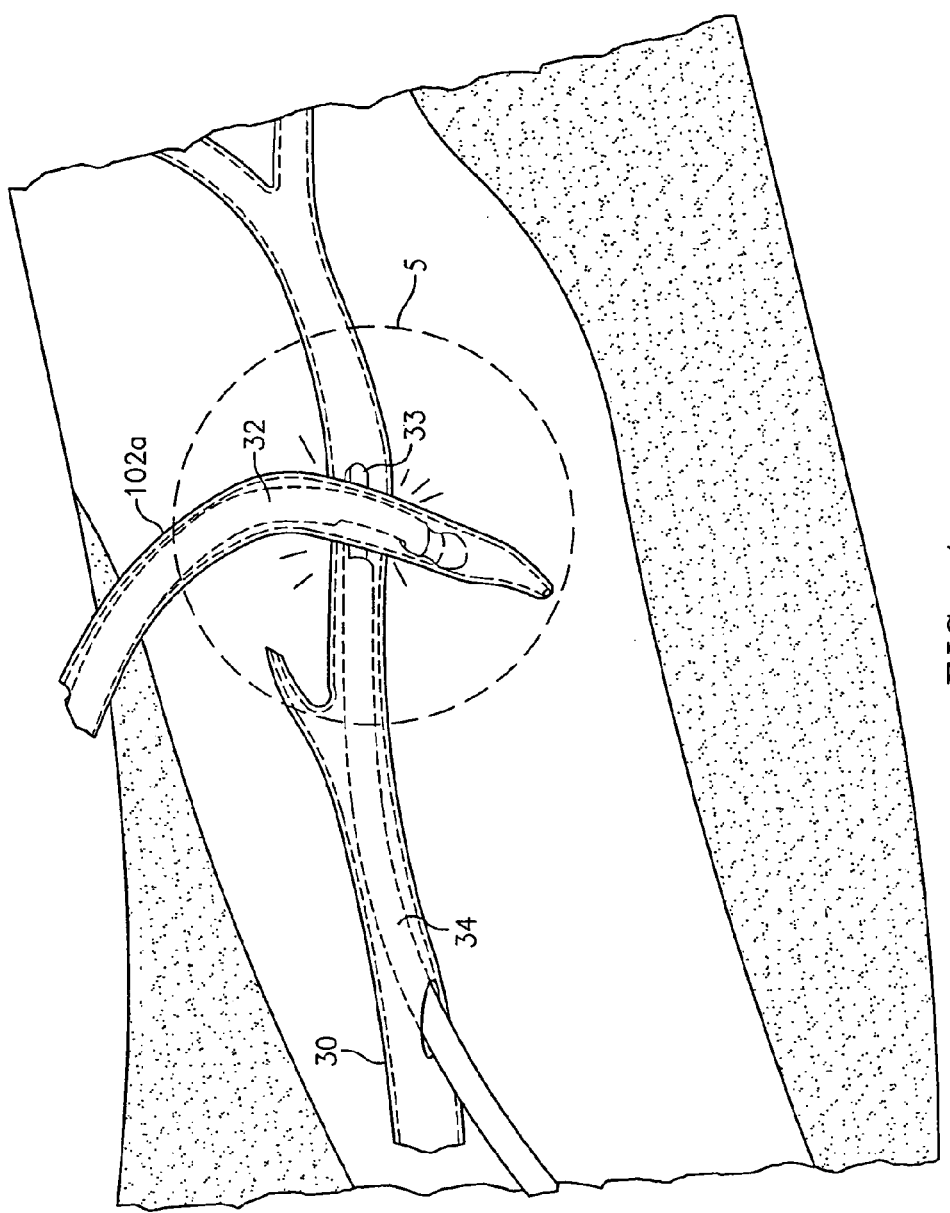
FIG. 4 shows accessing an artery in the forearm with a catheter and crossing one end of the cut vein over the artery.
Figure 5:
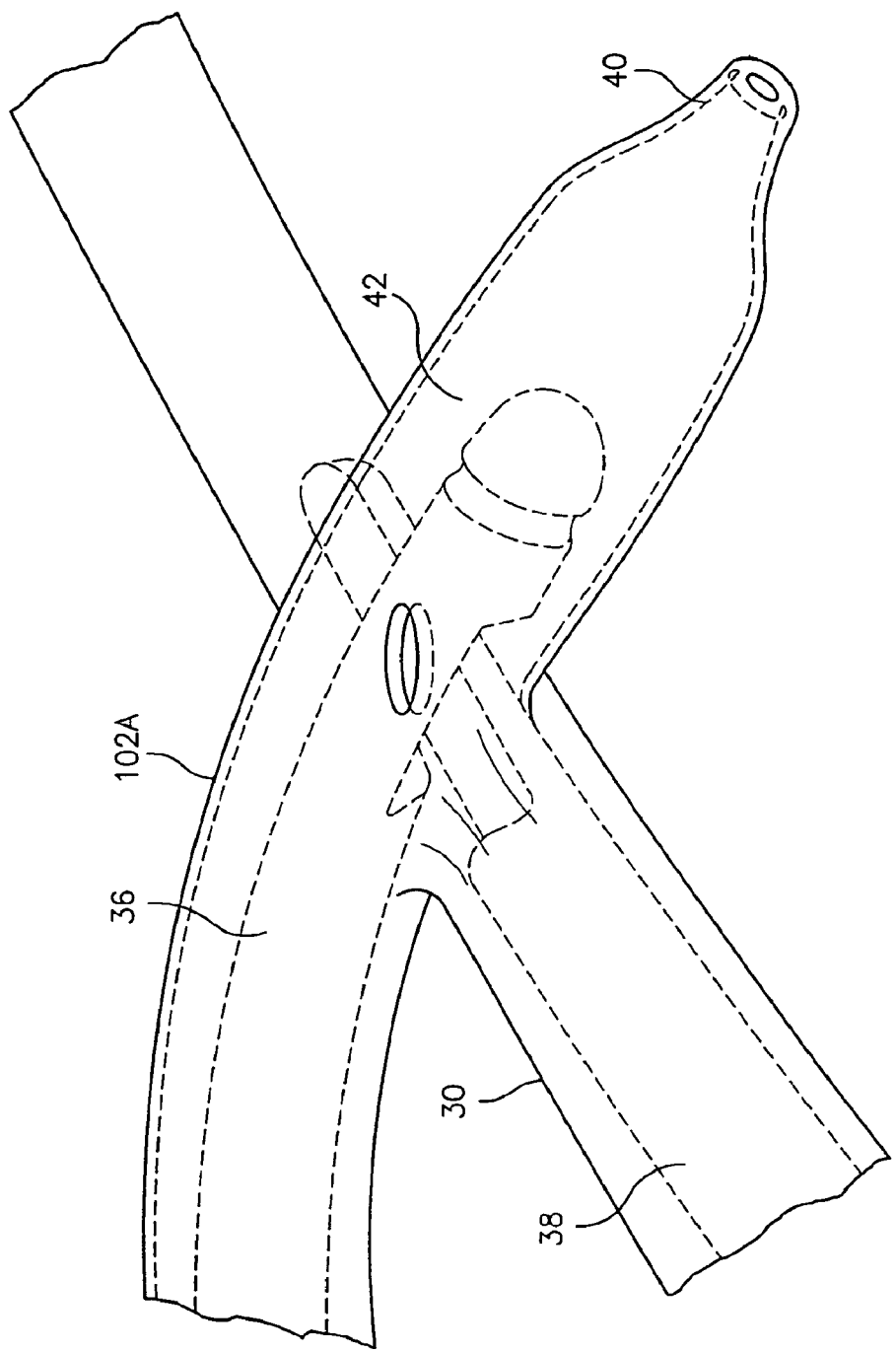
FIG. 5 shows the introduction of electrode catheters into the crossed end of the cut vein and the adjacent artery, performing anastomosis, occluding the free end of the cut vein, and creating a lumen between the bonded vein and artery.
Figure 6:
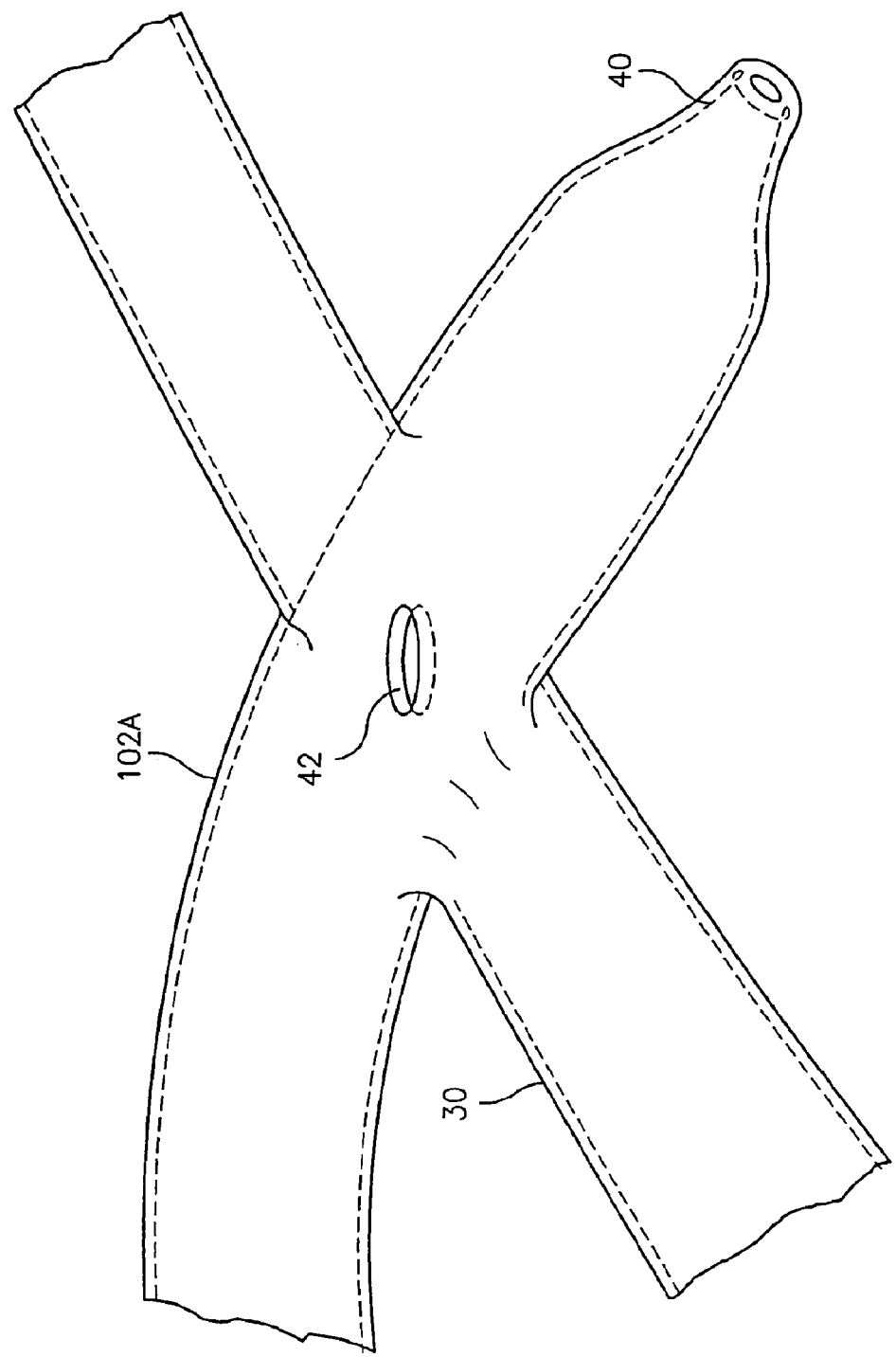
FIG. 6 shows the resultant structure with catheters removed.

A second phase in creating a native fistula is to make a connection between the cut vein and an artery, which is illustrated in FIGS. 4-6. A cut end of the vein, such as cut end portion 102A, is brought into contact with a selected artery, such as artery 30 shown in FIG. 4. As mentioned, it is advantageous that the vein and artery be adjacent each other; however, it should be understood that a connection can be made between a separated vein and artery not adjacent to one another by stripping away connective tissue from the vein and relocating the position of the vein. FIG. 4 illustrates a side-to-side connection, although certainly an end-to-side connection is also possible and contemplated by the present invention. The first cut end 102A of vein 102 is mobilized with catheter 32, and the artery 30 is accessed with catheter 34. If desired, a light 33 can be provided at the end of catheter 34 that is visible through the skin, and also at the end of catheter 32, if desired, in order to assist in locating or aligning the vein with respect to the artery. Naturally, other alignment means or visualization techniques know to one of skill in the art can be used, including fluoroscopy, radiopaque markers, ultrasound, etc.

In one variation of the present invention, radiofrequency (RF) energy is utilized to heat and fuse the vessels together. Tissue welding can be accomplished with heat and pressure between two collagen structures. The vein and artery outer layers or adventitia are composed primarily of collagen. When heated to between about 50° C. and 100° C. the collagen protein is denatured which allows it to be reformed or fused together. In addition, the strong fascia between the vein and artery is collagen, which is quite pronounced in the wrist area, and provides a welding medium to assist in achieving a better bond. Thus, as shown in FIG. 5, a vein electrode catheter 36 may be introduced into the first cut end 102A and an artery electrode catheter 38 may be introduced into artery 30 to perform an anastomosis between the first cut end 102A and artery 30. In one variation, this procedure includes the occlusion of the free end of first cut end 102A at first end portion 40, followed by the creation of a lumen 42 by connecting first cut end 102A of vein 102 with artery 30 along the sides thereof. The final structure can be seen in FIG. 6. RF energy may also be used to occlude the second end portion 44 of second cut end 102B (FIG. 8).

Figure 9:
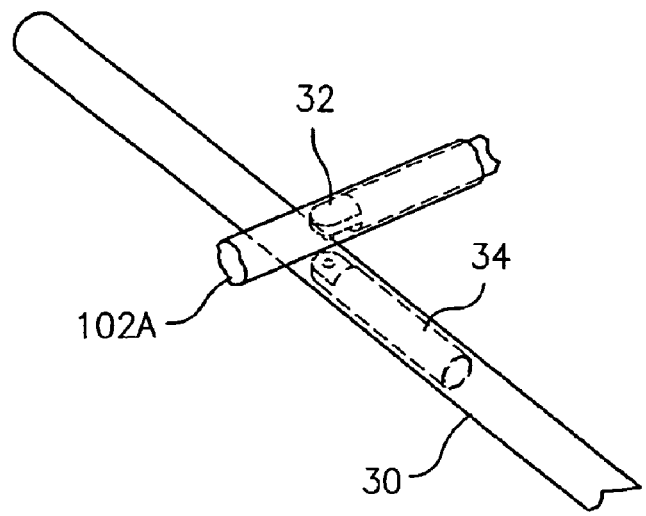
FIG. 9 is a detail view of the RF electrodes positioned in the adjacent vein and artery.
Figure 10:
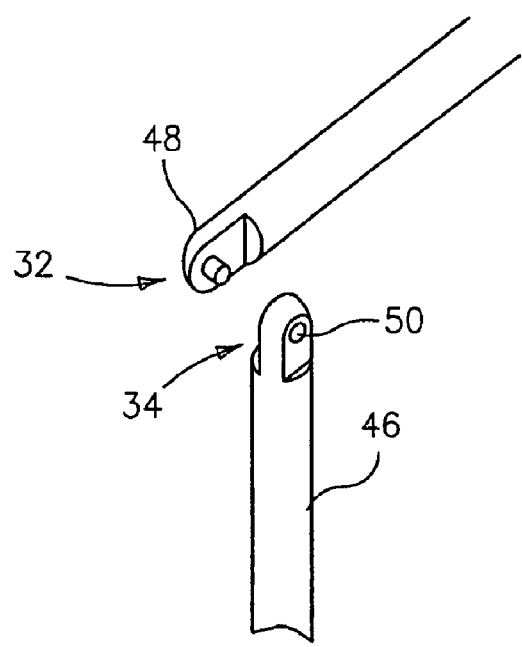
FIG. 10 is a detail view of the RF electrodes.

FIGS. 9 and 10 show vein electrode 32 and artery electrode 34, with FIG. 9 showing the electrodes in position in vein 102 first cut end 102A and in artery 30, and FIG. 10 showing the electrodes removed from the vessels with insulation 46 thereover. Alignment means may be provided on the RF electrodes to aid in alignment for the anastomosis, as for example post 48 on electrode 32 and opening 50 on electrode 34. Naturally other alignment means can be provided and are within the scope of this invention. RF energy at a frequency of from approximately 400 to 600 KHz, and generally at a frequency of about 500 KHz, is used in one embodiment of the present invention. In one variation, bi-polar RF energy is utilized and the desired tissue is simply positioned between the two electrodes as shown. The current flows from one electrode, through the tissue which has a resistance, to the other electrode. The resistance of the tissue produces the heat which fuses the tissues together and also forms the desired lumen. Pressure may be applied between the electrodes. Following the procedure, pressure is released after a cooling period and the electrode catheters are withdrawn, leaving the vein attached to the artery.

Thus, the present invention advantageously transects the vein in a simple, convenient manner, and bonds the vein to the artery and forms a lumen therebetween, also in a simple and convenient manner.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:
1. A blood vessel transecting device, comprising:
a cutting tool including:
a generally cylindrical first portion including a cutting element adapted to be exposed to an internal surface of a blood vessel in a cutting tool open position, and to be shielded from the blood vessel internal surface in a cutting tool closed position; and
a generally cylindrical second portion including an anvil that is movable with respect to the cutting element, the cutting element configured to rotate against the anvil to transect the blood vessel;
a catheter shaft coupled to the cutting tool; and
an occlusion device distal the cutting element, wherein the first portion is closer to the occlusion device in the open position and further away from the occlusion device in the closed position; and a suction means connected to the catheter shaft configured to apply a suction through an inner lumen of the catheter shaft.

2. The blood vessel transecting device according to claim 1, wherein the cutting element is cylindrical.

3. The blood vessel transecting device according to claim 1, wherein the first portion and the second portion contact in the closed position to form a generally uniform cylindrical body portion.

4. The blood vessel transecting device according to claim 1, wherein the first portion is distal the second portion.

5. The blood vessel transecting device according to claim 4, wherein the second portion and the occlusion device remain relatively fixed as the first portion transitions between the open position and the closed position.

6. The blood vessel transecting device according to claim 5, wherein the cutting element is positioned on a perimeter of the first portion.

7. The blood vessel transecting device according to claim 1, wherein the cutting element is positioned on a perimeter of the first portion.

8. The blood vessel transecting device according to claim 1, wherein a sharpened end of the cutting element directly contacts the anvil in the closed position.

* * * * *